Figure 1:
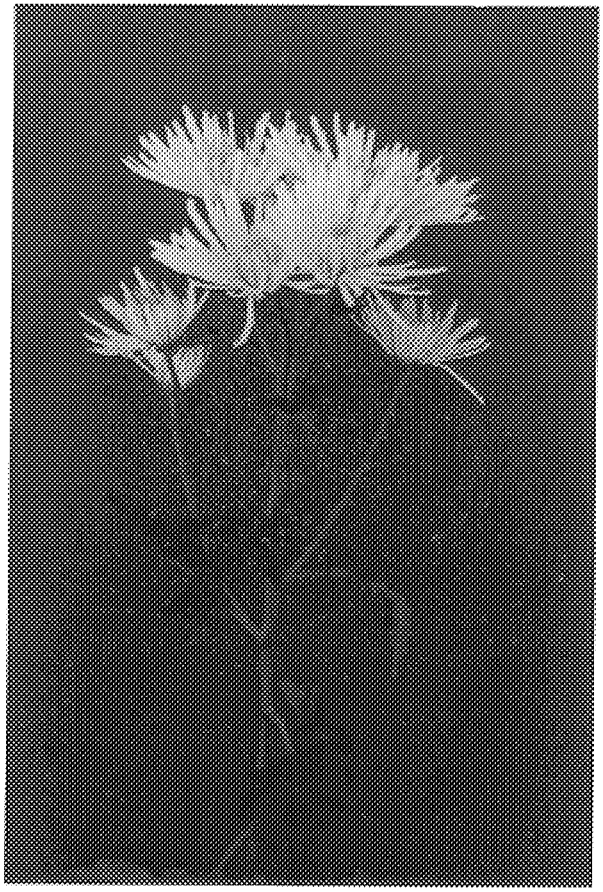

US00PP10604P

United States Patent [19]

VandenBerg

[11] Patent Number: Plant 10,604

[45] Date of Patent: Sep. 15, 1998

[54] CHRYSANTHEMUM PLANT NAMED 'SPOKANE'

[75] Inventor: Cornelis P. VandenBerg, Salinas, Calif.

[73] Assignee: Yoder Brothers, Inc., Barberton, Ohio

[21] Appl. No.: 842,071

[22] Filed: Apr. 23, 1997

[51] Int. Cl.[6] ..... A01H 5/00

[52] U.S. Cl. ..... Plt./77

[58] Field of Search ..... Plt./77, 78

*Primary Examiner*—Howard J. Locker

*Attorney, Agent, or Firm*—C. A. Whealy

[57] ABSTRACT

A distinct cultivar of Chrysanthemum plant named 'Spokane', characterized by its medium-sized quilled decorative-type inflorescences that are about 8 cm in diameter; pure white ray floret color; numerous ray florets per inflorescence; and exceptional postproduction longevity with flowering stems maintaining good substance and color for about four weeks in an interior environment after one week of cool storage.

3 Drawing Sheets

The present invention relates to a new and distinct cultivar of Chrysanthemum plant, botanically known as *Dendranthema grandiflora* and referred to by the cultivar name 'Spokane'.

The new cultivar is a product of a planned breeding program conducted by the inventor in Salinas, Calif. The objective of the breeding program is to create new Chrysanthemum cultivars having inflorescences with desirable colors and good form and substance.

The new cultivar originated from a cross made by the inventor in January, 1993, in Salinas, Calif. of two unnamed propietary seedling selections. The female parent, seedling number 0234, is a decorative-type cut Chrysanthemum with light pink ray florets. The male parent, seedling number 3693, is a quilled decorative-type cut Chrysanthemum with light pink ray florets.

The cultivar Spokane was discovered and selected by the inventor as a flowering plant within the progeny of the stated cross in a controlled environment in Alva, Fla., in April, 1994. The selection of this plant was based on its desirable inflorescence color and good form and substance.

Asexual reproduction of the new cultivar by terminal cuttings taken in a controlled environment in Alva, Fla., has shown that the unique features of this new Chrysanthemum are stable and reproduced true to type in successive generations.

The cultivar Spokane has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Spokane'. These characteristics in combination distinguish 'Spokane' as a new and distinct cultivar:

1. Medium-sized quilled decorative-type inflorescences that are about 8 cm in diameter.
2. Pure white ray floret color.
3. Numerous ray florets per inflorescence.
4. Exceptional postproduction longevity with flowering stems maintaining good substance and color for about four weeks in an interior environment after one week of cool storage.

The new Chrysanthemum is similar in ray floret color and type to the Chrysanthemum cultivar 'Traviata' (disclosed in U.S. Plant patent application Ser. No. 08/702,295). However in side-by-side comparisons in Salinas, Calif., under commercial practice, plants of the new Chrysanthemum differ from plants of the cultivar 'Traviata' in the following characteristics:

1. Flowering stems of the new Chrysanthemum are about 10 cm shorter than flowering stems of the cultivar 'Traviata'.
2. Flowering stems of the new Chrysanthemum flower 3 to 4 days earlier than flowering stems of the cultivar 'Traviata'.
3. Plants of the cultivar 'Traviata' have flattened inflorescences whereas ray florets of the new Chrysanthemum are more upright giving inflorescences a V-shape from a side perspective view.
4. Plants of the cultivar 'Traviata' can be grown as either disbuds or natural sprays whereas plants of the new Chrysanthemum are best grown as natural sprays.

The accompanying colored photographs illustrate the overall appearance of the new cultivar, showing the colors as true as it is reasonably possible to obtain in colored reproduction of this type.

FIG. 1 comprises a side perspective view of a typical flowering stem of 'Spokane' grown as a natural spray cut Chrysanthemum.

Figure 2:
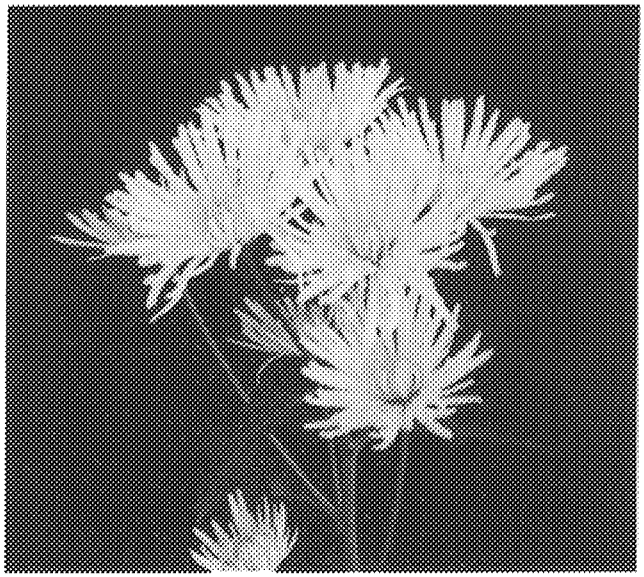

FIG. 2 comprises a side perspective view of typical inflorescences of the cultivar 'Spokane'.

Figure 3:
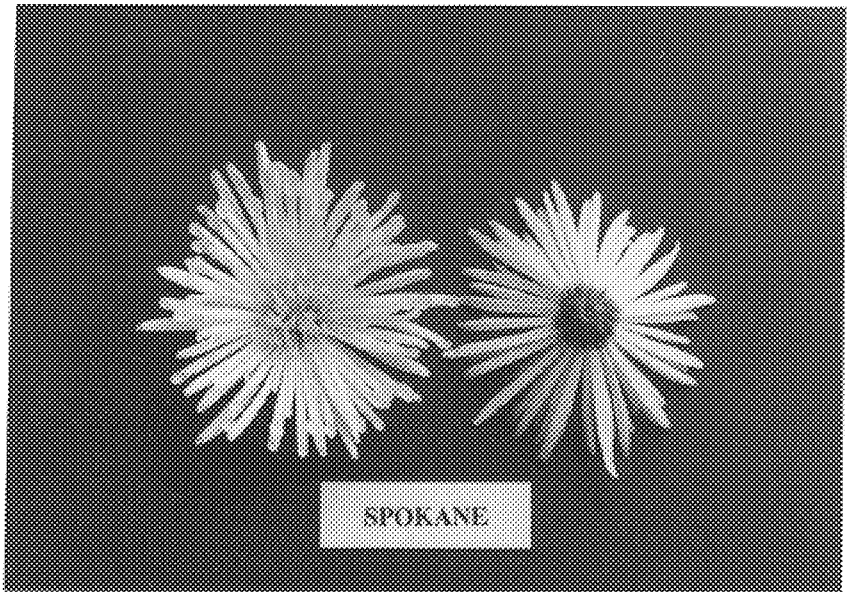

FIG. 3 comprises a top perspective view of adaxial (left) and abaxial (right) surfaces of typical inflorescences of the cultivar Spokane.

Figure 4:
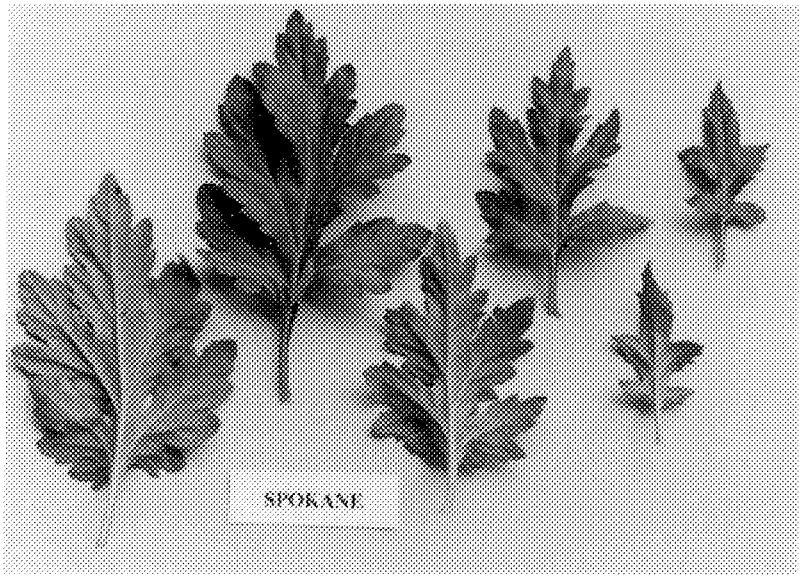

FIG. 4 comprises a top perspective view of the adaxial (top of photograph) and abaxial (bottom of photograph) surfaces of leaves of the cultivar 'Spokane' at three different stages of development showing the differences in size and lobation development.

Floret and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Salinas, Calif., under commercial practice in a polyethylene-covered greenhouse. Rooted cuttings were planted Nov. 7, 1996 and cut flowers were harvested on Jan. 13, 1997. After planting rooted cuttings of the new cultivar, plants received two weeks of long day/short nights following by short day/long nights until flowering. Measurements and numerical values represent averages for six typical flowering stems.

Botanical classification: *Dendranthema grandiflora* cultivar 'Spokane'.

Commercial classification: Quilled decorative spray-type cut Chrysanthemum.

Parentage:

*Male or pollen parent*.—Unnamed proprietary *Dendranhema grandiflora* seedling selection number 3693.

*Female or seed parent*.—Unnamed proprietary *Dendranthema grandiflora* seedling selection number 0234.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous quilled decorative spray-type cut flower. Stems upright, uniform habit and freely branching.

*Flowering stem length*.—About 79 cm.

*Foliage description*.—Leaf arrangement: Alternate. Leaf size, fully expanded: Length: About 10 cm. Width: About 7.75 cm. Leaf apex: Cuspidate. Leaf base: Attenuate. Leaf margin: Palmately lobed. Leaf texture; Abaxial and adaxial surfaces slightly pubescent. Veins prominent on abaxial surface. Color: Young foliage adaxial surface: 147A. Young foliage abaxial surface: 147B. Mature foliage adaxial surface: 147A. Mature foliage abaxial surface: 147B. Venation abaxial surface: 147B. Venation adaxial surface: 147B. Petiole: Length: About 3 cm. Color: 147B.

Flowering description:

*Appearance*.—Quilled decorative-type inflorescence form. Ray florets mostly upright giving inflorescences a V-shape from a side perspective view. Inflorescences borne on terminals, arising from leaf axils. Disc and ray florets arranged acropetally on a capitulum.

*Flowering response*.—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower 51 to 54 days later.

*Postproduction longevity*.—In an interior environment, flowering stems will maintain good color and substance for at about four weeks in an interior environment after one week of cool storage.

*Quantity of inflorescences*.—About 7 inflorescences per flowering stem.

*Inflorescence size*.—Diameter: About 8 cm. Depth (height): About 1.7 cm. Diameter of capitulum: About 5 mm.

*Ray florets*.—Shape: Quilled. Size: Length: About 4.25 cm. Width: About 3.5 mm. Apex: Dentate. Texture: Satiny, smooth, glabrous. Aspect: Mostly upright. Number of ray florets per inflorescence: About 237. Color: When opening: 154D to 150D with 154A at base. Mature: 155D with 154A at base.

*Disc florets*.—Disc florets rarely observed.

*Peduncle*.—Aspect: Strong and angled about 45° to the stem. Length: First peduncle: About 2.5 cm. Fourth peduncle: About 8 cm. Seventh peduncle: About 10 cm. Texture: Pubescent. Color: 147B.

*Reproductive organs*.—Without disc florets, androecium not observed. Gynoecium color: 154A.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Spokane', as illustrated and described.

* * * * *